United States Patent [19]

Graiver et al.

[11] Patent Number: 4,891,389

[45] Date of Patent: Jan. 2, 1990

[54] SOLID GEL DISPENSERS FOR ACHIEVING CONTROLLED RELEASE OF VOLATILE LIQUID MATERIALS AND METHOD FOR PREPARING SAME

[75] Inventors: Daniel Graiver, Midland; Robert E. Kalinowski, Auburn, both of Mich.

[73] Assignee: Dow Corning Corporation, Midland, Mich.

[21] Appl. No.: 371,481

[22] Filed: Jun. 26, 1989

Related U.S. Application Data

[60] Division of Ser. No. 337,671, Apr. 13, 1989, which is a continuation-in-part of Ser. No. 309,280, Jan. 26, 1989, abandoned.

[51] Int. Cl.⁴ .................................................. C08J 9/28
[52] U.S. Cl. .......................................... 521/64; 521/82; 521/88; 521/89; 521/134; 521/141
[58] Field of Search ............... 521/64, 134, 82, 89, 521/88, 141

[56] References Cited

U.S. PATENT DOCUMENTS

| | | | |
|---|---|---|---|
| 4,094,119 | 6/1978 | Sullivan | 53/400 |
| 4,117,110 | 9/1978 | Hautmann | 424/76 |
| 4,356,969 | 11/1982 | Overmeyer et al. | 523/102 |
| 4,594,380 | 6/1986 | Chapin et al. | 523/102 |
| 4,663,358 | 5/1987 | Hyon et al. | 521/64 |
| 4,719,040 | 1/1988 | Traas et al. | 512/4 |
| 4,720,409 | 1/1988 | Spector | 428/46 |

FOREIGN PATENT DOCUMENTS

| | | |
|---|---|---|
| 1617995 | 4/1971 | Fed. Rep. of Germany . |
| 2239255 | 4/1975 | France . |
| 2585954 | 2/1987 | France . |
| 147536 | 7/1988 | Japan . |
| 1544221 | 4/1979 | United Kingdom . |

*Primary Examiner*—Morton Foelak
*Attorney, Agent, or Firm*—Robert Spector

[57] ABSTRACT

Aesthetically attractive, free standing dispensers for the controlled release of volatile liquid materials such as perfumes and fragrances into the atmosphere consist essentially of composite hydrogels comprising a continuous phase of a solubilized polyvinyl alcohol, a dispersed phase comprising a polyelectrolyte and an aqueous solution of the volatile liquid that is distributed between said continuous and dispersed phases. The exterior surfaces of the dispenser remain dry to the touch throughout its useful life.

3 Claims, No Drawings

SOLID GEL DISPENSERS FOR ACHIEVING CONTROLLED RELEASE OF VOLATILE LIQUID MATERIALS AND METHOD FOR PREPARING SAME

REFERENCE TO RELATED APPLICATIONS

This is a divisional of co-pending application Ser. No. 337,671 filed on Apr. 13, 1989, which is a continuation-in-part of copending application Ser. No. 309,280, filed on Jan. 26, 1989, now abandoned.

BACKGROUND OF THE INVENTION

1. Field of the Invention

This invention relates to the controlled release of volatile materials. More particularly, this invention relates to improved dispensers for volatile liquid materials such as an air freshener fragrance or a biologically active composition. The dispenser consists essentially of a solid polyvinyl alcohol hydrogel containing a dispersed polyelectrolyte and an aqueous solution of the volatile material.

2. Description of the Prior Art

Dispensers for the controlled release of volatile liquids such as perfumes, deodorants and biologically active compositions are known. One class of dispensers comprise a matrix, such as a film formed from a natural or synthetic organic polymer, that is impregnated with the material to be released. Dispensers of this type are described in U.S. Pat. No. 4,720,409, which issued on Jan. 19, 1988. One major disadvantage of this type of dispenser is the relatively small volume of liquid that can be incorporated into a solid film of an organic polymer without destroying the coherency of the film. This severely limits the useful life of the dispenser.

A second type of controlled release dispenser comprises a reservoir of the volatile liquid material enclosed within either a rigid or flexible container wherein at least a portion of the wall of the container is porous to the volatile liquid. Dispensers of this type are described in U.S. Pat. No. 4,356,969, which issued on Nov. 2, 1982. To reduce the likelihood of leakage of a bulk liquid from the dispenser, the liquid composition containing the volatile materials to be released can be absorbed into a porous material such as a sponge or a polyurethane foam. The impregnated material can optionally be enclosed within a porous container. Dispensers of this type are described in West German Pat. No. 1,617,995, which issued on Apr. 22, 1971; French Pat. No. 2,585,954, which issued on Feb. 13, 1987; U.S. Pat. No. 4,594,380, which issued on Jun. 10, 1986; U.S. Pat. No. 4,094,119, which issued on Jun. 13, 1978; French Pat. No. 2,239,255, which issued on Apr. 4, 1975; and French Pat. No. 2,229,425, which issued on Jan. 17, 1975.

In a third type of dispenser the liquid composition containing the material to be released is incorporated into a gel or wax formed from a natural or synthetic organic polymer. Additives to modify the properties of the gel or wax can also be included in the composition.

U.S. Pat. No. 4,117,110, which issued on Sept. 26, 1978, describes an improved solid air deodorant wherein the active ingredient, typically a perfume composition, is combined with paraffin that has been gelled using a metallic soap. The improvements alleged for this product are the presence of the soap, which acts as a support for the hydrocarbon gel, and the ability to select the volatility of the paraffin to achieve an evaporation of both the paraffin and the active ingredient, thereby leaving the external appearance of the dispenser unchanged.

U.S. Pat. No. 4,719,040, which issued on Jan. 12, 1988 teaches absorbing a perfume into a finely divided, water insoluble polymer and combining the resultant mixture with from 0.5 to 10 percent, based on the combined weight of all ingredients, of a gelling agent.

Published European patent application No. 138,844, which issued on May 2, 1985 teaches achieving continuous diffusion of perfume into the atmosphere by incorporating the perfume composition into a gelling agent such as carrageen or agar containing a mineral substance of fiber such as calcium sulfate, an aluminum silicate or sawdust.

In accordance with the teaching of British Pat. No. 1,544,221 a volatile material, such as an air freshener fragrance or an insecticide, is combined with a liquid hydrocarbon and a soap of a polyvalent metal, and the resultant composition is incorporated into a spongy gel formed from a lower alcohol and the sodium salt of a higher fatty acid such as stearic acid.

None of the aforementioned prior art gels is completely satisfactory as a dispenser for achieving controlled release of volatile liquids such as perfumes and biologically active compositions.

Two of the most objectionable disadvantages of many prior art gels as dispensers for the controlled release of volatile materials are a wet or otherwise aesthetically unattractive surface and/or the slow rate at which the volatile materials are released from the gel.

When many prior art gels are used to dispense a fragrance or other volatile liquid the gel must be enclosed in a suitable container that conceals the gel and makes it inaccessible to the user of the dispenser, yet allows the volatile liquid to be released into the atmosphere at the desired rate. When the volatile liquid is an air freshener fragrance it is often desirable to have a relatively high initial rate of release, in the order of about 1 gram per hour which then gradually decreases over a period of several hours to a lower rate that is maintained over the useful life of the dispenser.

The preparation of some prior art gels requires blending a number of ingredients in specified proportions to achieve the desired release rate. In other instances the desired release rate cannot be achieved and/or maintained over the entire useable life of the dispenser, or not all of the volatile liquid is capable of being dispensed.

Gels prepared from solutions of polyvinyl alcohol (PVA) in water or a mixture of water and a water-miscible organic solvent such as methanol, propanol, dimethyl sulfoxide and N,N-dimethylformamide are disclosed in numerous patents and other publications. Typical of recently issued patents describing gels formed from aqueous solutions of polyvinyl alcohol is U.S. Pat. No. 4,663,358, which issued to Hyon et al on May 5, 1987. This patent teaches cooling to below room temperature a solution of polyvinyl alcohol in a mixture of water and a water-miscible organic solvent such as alcohols containing from 1 to 4 carbon atoms, glycols and dimethyl sulfoxide. Mixtures of water and dimethyl sulfoxide are preferred, and the water can constitute from 10 to 90 weight percent of the solvent mixture. The gel formed by cooling the solution is then immersed in flowing water to remove the organic solvent. Alternatively the initial gel is dried to remove substantially all of the solvent and then immersed in water to form the hydrogel. This patent also teaches that extraction of the organic solvent may not be necessary for certain end-use applications of the gel, including the controlled release of drugs or perfumes.

The alleged advantage of hydrogels prepared as described in the Hyon patent is their transparency relative to the opaque gels obtained from solutions of polyvinyl alcohol in either water or dimethyl sulfoxide as the only solvent.

The Hyon patent teaches that hydrogels prepared in accordance with the method disclosed in this patent differ from hydrogels prepared at room temperature by the absence of stickiness and improved mechanical strength. The hydrogels are capable of being molded into articles of various shapes, however there is no indication regarding whether the aesthetic properties of the gel other than stickiness differ from those of other prior art gels, specifically, whether any liquid is initially present on the surface of the molded article or exudes to the surface when the article is exposed to the atmosphere for extended periods of time under ambient conditions. If the gel is to be used as a free standing dispenser for the controlled release of a perfume or other volatile material over a period of days or weeks, the presence of liquid materials during this period would be aesthetically unacceptable to the user of such a dispenser.

U.S. patent application Ser. No. 309,280, filed on Jan. 26, 1989 in the names of the present inventors discloses that controlled release dispensers prepared using PVA hydrogel compositions of the type described in the aforementioned Hyon et al. patent are unique with respect to dispensers formed from other hydrogels by virtue of surfaces that remain dry to the touch throughout the useful life of the dispenser. Unlike prior art dispensers, the dispensers described in the aforementioned application are aesthetically attractive in addition to being free standing, and therefore do not have to be enclosed in a container to conceal the gel and/or prevent leakage of liquid materials that appear on the surface of the dispenser as the volatile material(s) entrapped within the dispenser is released. An advantage of these dispensers is the ability to mold the gel from which the dispenser is prepared into any desired shape.

One disadvantage of hydrogels formed from polyvinyl alcohol is that the amount of aqueous composition capable of being incorporated into the hydrogel is limited to about 90 weight percent, based on the total weight of the hydrogel.

U.S. patent application Ser. No. 371,481, filed on Jun. 26, 1989, in the names of D. Graiver, E. Gen and Y. Ikada discloses composite polyvinyl alcohol hydrogel compositions containing a dispersed phase of a polyelectrolyte such as sodium polyacrylate. These composite hydrogels are capable of absorbing considerably larger amounts of water relative to prior art polyvinyl alcohol hydrogels. These hydrogels expand up to 8000% or more in the presence of water without loss of structural integrity.

SUMMARY OF THE INVENTION

In accordance with one aspect of this invention aesthetically attractive, free standing dispensers for the controlled release of volatile liquid materials such as perfumes and fragrances into the atmosphere are prepared by (1) forming a first aqueous composition comprising a solubilized polyvinyl alcohol, water, a polyelectrolyte and an amount of a water-miscible liquid sufficient to maintain said polyelectrolyte as a dispersed phase while avoiding precipitation of the polyvinyl alcohol, said water-miscible liquid being selected from the group consisting of monohydric alcohols and dimethyl sulfoxide, (2) cooling the resultant aqueous composition to below room temperature to form a hydrogel in the shape of the final dispenser, (3) when dimethyl sulfoxide is an ingredient of said aqueous composition, immersing the hydrogel in methanol for a sufficient time to extract said dimethyl sulfoxide, and then (4) immersing said hydrogel in a second aqueous composition comprising water, said volatile liquid material and a monohydric alcohol containing from 1 to about 3 carbon atoms in an amount sufficient to solubilize the volatile ingredient.

The present dispensers contain up to 99 weight percent of a aqueous mixture containing the volatile liquid material, which is dispensed at a uniform, controllable rate into the atmosphere adjacent to the dispenser. The surface of the dispenser remains dry to the touch throughout the dispensing process.

DETAILED DESCRIPTION OF THE INVENTION

This invention provides an improved dispenser for achieving controlled release over an extended period of time of a volatile liquid into the environment adjacent to the dispenser, the dispenser comprising a hydrogel formed from an aqueous solution of polyvinyl alcohol. The improvement comprises (1) the presence in said hydrogel of from 1 to 20 percent, based on the total weight of said hydrogel, of a polyelectrolyte that is present as a finely divided dispersed phase within a continuous phase of said hydrogel, and a monohydric alcohol containing from one to four carbon atoms in an amount sufficient to solubilize said volatile liquid and without precipitating the polyvinyl alcohol, (2) a method for preparing said dispenser whereby at least a portion of said volatile liquid is incorporated into said dispenser by immersing it in an aqueous mixture comprising said volatile liquid and (3) a free standing dispenser possessing an exterior surface that is initially dry to the touch and remains so throughout the useful life of said dispenser.

The characterizing features of this invention include (1) a dispenser that is free standing, remains dry to the touch throughout its useful life and is fabricated from a hydrogel comprising a continuous phase containing from 5 to 25 percent, based on the weight of said dispenser, of a solubilized polyvinyl alcohol (PVA) and a finely divided dispersed phase containing from 1 to 20 percent, based on the weight of said dispenser, of a polyelectrolyte, and (2) up to 99 percent, based on the total weight of the hydrogel, of an aqueous composition comprising water, a volatile liquid to be released from said dispenser and at least one water-miscible aliphatic monohydric alcohol containing from 1 to about 4 carbon atoms, the concentration of said alcohol being sufficient to solubilize said volatile liquid.

THE POLYVINYL ALCOHOL (PVA) PORTION OF THE HYDROGEL

The polyvinyl alcohol that comprises the polymer portion of the continuous phase in the present dispensers is typically prepared by hydrolysis or saponification of polyvinyl acetate. The degree of hydrolysis varies depending upon the intended end use of the polymer.

The vinyl alcohol polymers of this invention are preferably fully hydrolyzed and are linear or contain at most a minimal degree of branching. The reason for this preference is to achieve the maximum degree of hydrogen bonding. The formation of hydrogen bonding between hydroxyl groups on adjacent polymer molecules and crystallization of the polymer are considered responsible for the development of the excellent physical properties associated with this type of polymer.

The molecular weight of the PVA used to prepare the gel and, ultimately, the dispenser is determined by the desired physical and aesthetic properties of the dispenser. The molecular weight of the PVA should not be less than 44,000, preferably not less than 75,000. Commercially available polymers with molecular weights of from 75,000 to 440,000 are preferred for preparing the present dispensers, particularly those polymers containing relatively large concentrations of syndiotactic or isotactic segments within the polymer molecules.

To maximize the concentration of active ingredient, i.e. the fragrance or other volatile liquid, in the dispenser the concentration of PVA in the initial solution should be as low as will allow formation of a hydrogel that retains its integrity and a dry surface in the presence of the solubilized active ingredient. The operable and preferred concentration ranges for the PVA will be at least in part dependent upon the molecular weight of this polymer.

Typically the properties of PVA gels, particularly tensile strength and elongation at break, increase with increasing concentration and/or molecular weight of the polymer. PVA concentrations of below about 10 weight percent are preferred, although higher concentrations of polymer can be used if it is desired to improve physical properties at the cost of reducing the concentration of liquid ingredients in the final dispenser.

THE POLYELECTROLYTE PHASE OF THE HYDROGEL

The ability of the present dispensers to absorb an amount of water equal to up to 8000 times the weight of the polymeric ingredients present in the hydrogel is due to the presence of a polyelectrolyte that is present as a finely divided dispersed phase within a matrix of solubilized polyvinyl alcohol.

Suitable polyelectrolytes are capable of being ionized and dissociated on contact with water, but are insoluble in the liquid PVA compositions used to prepare the present hydrogels and dispensers. Examples of suitable polyelectrolytes include but are not limited to polyacrylic acid, polymethacrylic acid, sodium, potassium and other metal salts of polyacrylic acid and polymethacrylic acid, polyethyleneimine, polymethacrylamide, partially hydrolyzed polyacrylamide, partially hydrolyzed polyalkylacrylamide, polyphosphoric acid, polyethylenesulfonic acid, polystyrenesulfonic acid, polyvinylamine, polyvinylsulfonic acid, polyvinylpyridines, poly-2-acrylamido-2-methylpropanesulfonic acid, copolymers of monomers having an ionizable atomic group such as copolymers of vinyl alcohol and acrylic acid, water-soluble derivatives of natural substances, and polymers thereof. These polyelectrolytes can be used singly or in the form of mixtures of two or more of them. Alkali metal and alkaline earth metal salts, especially sodium salts, of polymerized ethylenically unsaturated acids such as acrylic acid are preferred.

The polyelectrolyte portion of the present hydrogels exists as a dispersed particulate phase within a matrix of PVA. The particle size range of the polyelectrolyte is typically from about 10 to about 50 microns. The presence of the polyelectrolyte as a discrete phase can be recognized when the water is removed from the hydrogel.

The polyelectrolyte is preferably crosslinked to the extent that it will expand but not dissolve when immersed in water. The reason for this preference is to avoid migration of the polyelectrolyte together with the liquid material that diffuses to the surface during release of the volatile liquid from the dispenser. Under these conditions the quantity of linear polyelectrolyte reaching the surface of the dispenser may be sufficient to impart a stick or tacky touch to the surface.

A second route by which composition of the hydrogel can be altered is by leaching out of water soluble linear polyelectrolytes when the dispenser is regenerated by standing in excess water. For certain end-use applications it may be desirable to refill the present gel dispensers when the initial supply of liquid materials is depleted. This is conveniently accomplished by immersing the depleted hydrogel in an aqueous solution of the volatile liquid and allowing the gel to expand as the solution is absorbed. This immersion process can be repeated when the initial supply of volatile liquid is depleted by evaporation.

Hydrogels containing the preferred cross linked polyelectrolytes can be subjected to more of these expanding and contracting cycles without significant changes in composition resulting from solubilization of the polyelectrolyte in the water that gradually diffuses out of the hydrogel as it contracts.

Another method for reducing loss of polyelectrolyte from the dispenser is to employ as the polyelectrolyte block copolymers containing a PVA block and a polyelectrolyte block. These block copolymers have a reduced tendency to diffuse out of the hydrogel composite during repeated expanding and contracting cycles because of the compatibility of the PVA block with the PVA present in the matrix portion of the present dispensers. It is believed that the PVA block forms hydrogen bonds with the PVA matrix in which the polyelectrolyte is dispersed. These hydrogen bonds act as anchors to hold the polyelectrolyte within the hydrogel matrix. Block copolymers of vinyl alcohol and acrylic acid and block copolymers of vinyl alcohol and methacrylic acid are preferred.

The total solids concentration and the weight ratio of polyelectrolyte to PVA will affect a number of properties of the present composite hydrogels, particularly the maximum amount of water the gel will absorb. To fully utilize the advantages of composite hydrogels for the controlled release of volatile liquids the hydrogel should contain the maximum amount of polyelectrolyte that will yield a self-supporting article. With the exception of the aforementioned block copolymers, a significant portion of non-crosslinked polyelectrolytes are leached out when the dispenser is placed in an aqueous solution of the volatile liquid. It is therefore possible to form self-supporting dispenser from compositions containing up to about 80 weight percent of these polyelectrolytes, based on the combined weight of polyelectrolyte and PVA. On the other hand, polyelectrolytes that are either crosslinked or block copolymers containing PVA segments are not readily leached out. The concentration of these polyelectrolytes is therefore limited to a maximum of about 70 percent, based on the combined weight of polyelectrolyte and PVA if the final dispenser is to be self-supporting.

FORMATION OF THE COMPOSITE HYDROGEL DISPENSER

Hydrogels of the present type can be prepared by uniformly dispersing the polyelectrolyte throughout a solution of PVA. The PVA is dissolved in a mixture of water and a water miscible liquid that can be dimethyl sulfoxide or a monohydric alcohol containing from 1 to 4 carbon atoms. The concentration of dimethyl sulfoxide or alcohol is sufficient to maintain the polyelectrolyte as a dispersed phase within the solubilized PVA without causing precipitation of the PVA. For dimethyl sulfoxide this concentration range is typically from 50 to about 85 weight percent, based on the combined weight of this solvent and water, while for alcohol this range is typically from 10 to about 40 percent by weight, preferably from 20 to 35 percent by weight. Alcohol concentration greater than about 40 weight percent often result in precipitation of the PVA.

The solution of PVA and dispersed polyelectrolyte in one of the aforementioned water/alcohol or water/DMSO mixtures is cooled to a temperature lower than 25° C., preferably below 0° C., to form a hydrogel. This low-temperature treatment promotes gelation, and yields a solid gel wherein the polyelectrolyte is dispersed in as finely divided solid particles within a PVA matrix. The container in which the solution is cooled preferably conforms to the shape of the final dispenser.

The cooling period required to form a hydrogel from the PVA solution is cooled depends upon a number of variables, including the concentration and molecular weight of the polymer, the rate at which the solution is cooled, and the rate at which the resultant gel is returned to ambient temperature. Taking all of these variables into account, this time period is generally from 2 to 16 hours.

The present inventors found that for the types and concentrations of polymers and the range of processing conditions they evaluated no significant additional improvement in properties of the final dispenser was apparent after 16 hours of cooling.

When the water miscible liquid present in the initial PVA solution is dimethyl sulfoxide (DMSO), the next step in preparing the present dispenser is replacement of the DMSO with a volatile alcohol such as methanol or ethanol by placing the hydrogel in contact with an excess of this alcohol. Typically the hydrogel is place in a container filled with the alcohol and allowed to remain there for a period of time sufficient to extract the DMSO. This time period is usually from 24 to 48 hours.

The final step in the method for preparing the present dispensers is to place the hydrogel, which is preferably in the form of the final dispenser, in an aqueous solution of the volatile liquid to be released during operation of the dispenser. If the volatile liquid is not soluble in water, the solution also contains an amount of a monohydric alcohol sufficient to solubilize the volatile liquid. Because the alcohol is not a swelling agent for the polyelectrolyte, and may thereby reduce the weight of liquid capable of being absorbed by the dispenser, the amount of alcohol should be limited to the minimum required to solubilize the volatile ingredient. Because many volatile ingredients, particularly fragrances and biologically active compounds, are not readily soluble in a water-alcohol mixture, one or more water-miscible organic compounds such as ketones or amides such as N,N-dimethylformamide and N,N-dimethylacetamide may also be required.

During this step of the process the dispenser may swell to 2 or more times its original volume.

As disclosed in preceding sections of this specification, the liquid ingredients constitute up to about 98 weight percent of the final hydrogel and the dispensers fabricated from these hydrogels. The maximum amount of liquid material will depend at least in part upon the relative concentrations of polyelectrolyte and water in the hydrogel.

The fragrance or other volatile active ingredient to be released from the present dispensers typically constitutes from about 5 to about 25 weight percent of the liquid, i.e. non-polymer, ingredients present in the dispensers of this invention. When the volatile material is a fragrance, a variety of both natural and synthetic floral and herbal fragrances are commercially available and can be used for this purpose.

An alternative method for preparing the final dispenser is cooling the initial PVA/polyelectrolyte mixture to form a rod or similarly shaped elongate article that is subsequently placed in the solution of volatile ingredient and allowed to swell, after which it is cut into pellets. Because the gel behaves as a thermoplastic material, the pellets can be melted and fabricated into the desired shape. The pellets themselves can be placed in a suitable decorative container having at least one aperture through which the volatile liquid contained within the hydrogel is released into the atmosphere.

The advantage of the present hydrogels containing up to 95 percent by weight or more of a solubilized volatile ingredient as the liquid phase is their ability to be used directly as a free standing dispenser for an air freshener fragrance or other volatile liquid. The gel does not have to be confined in a container to avoid leakage of liquid material and/or requiring the ultimate user of the dispenser to handle an exposed wet surface or view an aesthetically unattractive article at any time during the useful life of the dispenser. As disclosed in the preceding specification, the exterior surface of the initial dispenser is dry to the touch and remains dry until the all of the air freshener fragrance or other active ingredient has been released.

It should be apparent that the external dimensions of articles formed from the present air freshener compositions will decrease substantially as the mixture of active ingredient and volatile solvents evaporates into the atmosphere. Under given conditions of temperature and humidity the rate at which the active ingredient is released into the atmosphere will be directly proportional to the external dimensions of the dispenser. The reduction in external dimensions will cease when the supply of active ingredient is exhausted, thereby providing an obvious signal to the user that the useful life of the dispenser is complete. A second method for determining the end of the useful life is to include in the composition used to prepare the dispenser a small amount of a basic or acidic material and a pH indicator such as thymol blue that will undergo a color change within the pH range of from 5 to about 8. The present inventors have found that the indicator will undergo a color change as the concentration of active ingredient approaches zero.

Volatile liquid materials other than perfumes and fragrances that can be released at a controlled rate using the PVA dispensers of this invention include but are not limited to deodorizers and physiologically or biologically active materials such as insect attractants or repellents, pheromones, disinfectants, pesticides, preservatives, and vaporized medications.

The following examples are intended to describe preferred embodiments of the present invention and should not be interpreted as limiting the scope of the invention as defined in the accompanying claims. Unless otherwise specified all parts and percentages specified in the examples are by weight and viscosities were measured at 25 degrees C.

EXAMPLE 1

This example describes the preparation of a preferred type of air freshener dispenser.

A dispenser of this invention was prepared by blending the following ingredients to homogeneity in a glass reactor equipped with a mechanically operated stirrer, water cooled condenser and thermometer:

15 parts of a polyvinyl alcohol with a degree of hydrolysis of at least 99.8 mole % and exhibiting a number average molecular weight of 86,000;
30 parts of a copolymer of polyvinyl alcohol and polyacrylic acid, available as SP-510 from Sumitomo Chemical as the polyelectrolyte;
228 parts dimethyl sulfoxide; and
57 parts water.

The resultant slurry was heated for 30 minutes at 100° C. to dissolve the polyvinyl alcohol. The polyelectrolyte remained dispersed in the solution. The composition was allowed to cool to 60° C., at which time it was poured into a mold fabricated from silicone rubber. The filled mold was then stored for about 16 hours in the freezer compartment of a residential type refrigerator-freezer that was maintained at a temperature of −20° C. The resultant molded dispenser of this invention, which was in the shape of a frog (Sample 1), was removed from the mold and placed into a methanol bath to extract the dimethyl sulfoxide. The methanol was replaced twice during a two-day period, following which the dispenser was removed from the bath and allowed to dry. The dispenser was then placed in a solution of a floral type fragrance dissolved in a 65/35 weight ratio mixture of water/ethanol. The dispenser was removed from the fragrance solution after 24 hours. The dispenser weighed 158 grams.

To determine the rate at which the fragrance and other volatile liquids were released the dispenser was allowed to remain under ambient conditions while the weight of the dispenser was measured periodically using an analytical balance. The rate of weight loss between each of the weight measurements was calculated and appears in Table 1. The dispenser remained dry to the touch throughout the entire testing period.

For purposes of comparison the rate of weight loss exhibited by a dispenser prepared without a polyelectrolyte was determined. The dispenser was prepared by blending to homogeneity 36 parts each of water and a finely divided polyvinyl alcohol (PVA) exhibiting a molecular weight of 86,000. The mixture was heated with stirring under ambient pressure. When the temperature reached 90° C., 60 parts of a solution of a floral type fragrance in a 65/35 weight ratio water/ethanol mixture was added to the reactor. The resultant mixture was heated at a temperature of 87° C. for about ten minutes until the polymer had completely dissolved, at which time 268 parts of the fragrance solution were added and heating was continued for an additional 20 minutes. An additional 19.38 parts of PVA and 19.4 parts of ethanol were then added to achieve a PVA concentration of 9.0% and a 65/35 weight ratio of water/ethanol in the final solution.

The PVA solution was allowed to cool to 60° C., at which time it was poured into the same mold used to prepare sample 1. The filled mold was then stored for about 64 hours in the freezer compartment of a residential type refrigerator-freezer that was maintained at a temperature of −20° C. The resultant dispenser was removed and tested for release rate. These data appear in Table 1 under the heading "Comparative Sample".

TABLE 1

| Sample 1 | | Comparative Sample | |
|---|---|---|---|
| Time (Hrs.) | Weight Loss Rate (Grams/Hour) | Time (Hrs.) | Weight Loss Rate (Grams/Hour) |
| 0.48 | 4.18 | 0.53 | 0.94 |
| 1.48 | 3.19 | 1.45 | 1.30 |
| 3.02 | 2.68 | 3.22 | 1.45 |
| 4.13 | 2.46 | 4.15 | 1.45 |
| 5.05 | 2.28 | 5.10 | 1.44 |
| 20.48 | 1.26 | 22.50 | 0.97 |
| 25.55 | 1.19 | 25.15 | 0.94 |
| 28.85 | 1.17 | 28.99 | 0.91 |
| 45.25 | 0.98 | 46.29 | 0.75 |
| 49.46 | 0.95 | 49.38 | 0.73 |
| 76.76 | 0.71 | 77.62 | 0.58 |
| 148.53 | 0.46 | 148.90 | 0.36 |
| 180.53 | 0.40 | 190.29 | 0.31 |
| 364.53 | 0.22 | 363.26 | 0.18 |
| 419.66 | 0.19 | 414.50 | 0.12 |
| 484.68 | 0.17 | 509.60 | 0.10 |

These data demonstrate that the initial release rate for the present dispenser was larger than the rate for the comparative sample by a factor of almost 5, and remained greater throughout the test period.

EXAMPLE 2

This example demonstrates the direct relationship between the ratio of polyvinyl alcohol to polyelectrolyte and the rate at which a volatile liquid composition is released from the present dispenser.

Three films were prepared by blending to homogeneity polyvinyl alcohol (PVA), the polyelectrolyte described in the preceding Example 1 (SP-510), dimethyl sulfoxide (DMSO) and water to form a slurry. The amounts of these ingredients used to prepare the three compositions are listed in Table 2. The slurry was heated for half an hour at a temperature of 100° C. then poured into a petri dish to form a 4.8 mm-thick layer. The compositions were gelled by placing the dishes in the freezer compartment of a residential refrigerator-freezer maintained at a temperature of −20° C. for about 16 hours. The resultant film was then placed in a container of methanol to extract the dimethyl sulfoxide. The methanol was replaced twice over a period of 48 hours. The films were then dried to remove the methanol and divided into samples weighing from 0.1 to 0.4 grams each. The weight of each sample was recorded prior to placing it into a solution of a floral type fragrance in a 65/35 weight ratio water/ethanol mixture and remained in this solution under ambient conditions until no additional increase in weight was observed, which required 7 days. The amount of fragrance solution absorbed during this period, expressed as a percentage of the weight of the film prior to being placed in the fragrance solution, is recorded in Table 2.

The samples were then allowed to remain under ambient conditions and weighed periodically to determined the amount of material that had been released. The percentage of the fragrance mixture remaining in each sample at each of these weighings was calculated. The calculated data are recorded in Table 3.

TABLE 2

| Sample | 2 | 3 | 4 |
| --- | --- | --- | --- |
| PVA (parts) | 10 | 10 | 5 |
| SP-510 (parts) | 2.5 | 5 | 10 |
| DMSO (parts) | 90 | 108 | 108 |
| Water (parts) | 22.5 | 27 | 27 |
| PVA/SP-510 | 4/1 | 2/1 | 1/2 |
| Percent Weight Increase During Liquid Absorption | 573 | 1046 | 3445 |

TABLE 3

| Elapsed Time (Hours) | Weight Percent of Liquid Remaining | | |
| --- | --- | --- | --- |
| | 2 | 3 | 4 |
| 0 | 100 | 100 | 100 |
| 6.82 | 27.27 | 56.56 | 70.46 |
| 22.60 | 2.27 | 17.21 | 49.63 |
| 31.28 | 2.27 | 6.56 | 28.98 |
| 46.47 | 0 | 1.23 | 12.22 |
| 54.47 | — | 0.82 | 6.82 |
| 118.47 | — | 0 | 0.71 |
| 126.19 | — | — | 0 |

That which is claimed is:

1. In a dispenser for achieving controlled release over an extended period of time of a volatile liquid selected from the group consisting of fragrances, disenfectants, biologically active materials, perfumes, deodorizers and physiologically and biologically active materials into the environment adjacent to the dispenser, the dispenser comprising a hydrogel formed from an aqueous solution of polyvinyl alcohol, the improvement comprising (1) the presence in said hydrogel of from 1 to 20 percent, based on the total weight of said hydrogel, of a polyelectrolyte which is capable of being ionized and dissociated on contact with water, but is insoluble in the liquid polyvinyl alcohol used to prepare said hydrogel, where said polyelectrolyte is present as a finely divided dispersed phase within a continuous phase of said hydrogel, and a monohydric alcohol containing from one to four carbon atoms in an amount sufficient to solubilize said volatile liquid and without precipitating the polyvinyl alcohol, (2) a method for preparing said dispenser whereby at least a portion of said volatile liquid is incorporated into said dispenser by immersing it in an aqueous solution of said volatile liquid and (3) a free standing dispenser possessing an exterior surface that is initially dry to the touch and remains so throughout the useful life of said dispenser.

2. A dispenser according to claim 1 where said volatile liquid is a fragrance, disinfectant or a biologically active material, the solvent for said polyvinyl alcohol is a mixture comprising water and an alcohol, where said alcohol constitutes less than 40 weight percent of said solvent, the molecular weight of the polyvinyl alcohol is from 75,000 to 440,000, the polyvinyl alcohol constitutes less than 10 percent by weight of said hydrogel, said polyelectrolyte is selected from the group consisting of alkali metal salts of ethylenically unsaturated acids and block copolymers of said salts and polyvinyl alcohol, the particle size of said polyelectrolyte is from 10 to 50 microns, the polyelectrolyte when uncrosslinked and substantially free of polyvinyl alcohol constitutes no more than about 80 percent of the combined weight of polyvinyl alcohol or no more than about 70 percent of said combined weight when crosslinked or in the form of a block copolymer containing polyvinyl alcohol segments, and said dispenser contains an acidic or basic material and a pH indicator that undergoes a color change within the pH range of from 5 to about 8 as a means for signaling the end of the useful life of said dispenser.

3. A dispenser according to claim 2 where said polyelectrolyte is crosslinked or is a copolymer comprising blocks of polyvinyl alcohol units and blocks of said polyelectrolyte, the polyelectrolyte is a block copolymer derived from an ethylenically unsaturated acid and polyvinyl alcohol, the volatile liquid is an air freshener fragrance, said alcohol is ethanol and is present at a concentration of from 20 to 35 weight percent, based on the weight of the solvent present in said final solution.

* * * * *